Figure 1:
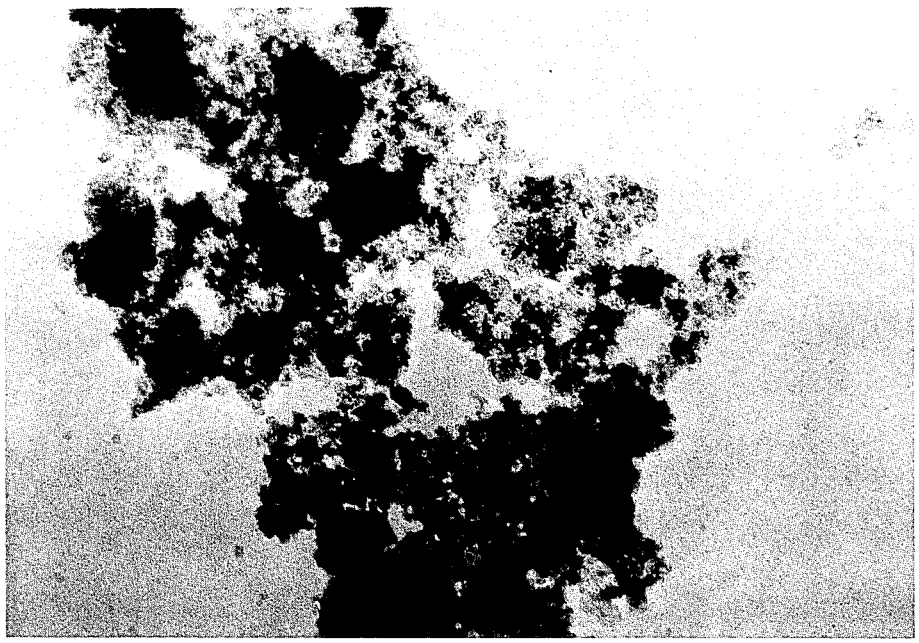

United States Patent [19]

Gradeff et al.

[11] Patent Number: 4,545,923
[45] Date of Patent: Oct. 8, 1985

[54] PROCESS FOR PREPARING COLLOIDAL CERIC OXIDE AND COMPLEXES THEREOF WITH FREE ORGANIC ACIDS

[75] Inventors: Peter S. Gradeff, Pottersville; Vincent J. Charte, East Windsor; Fred G. Schreiber, Highland Park; John F. Davison, Edison, all of N.J.

[73] Assignee: Rhone-Poulenc Inc., New Brunswick, N.J.

[21] Appl. No.: 460,694

[22] Filed: Jan. 24, 1983

Related U.S. Application Data

[63] Continuation-in-part of Ser. No. 387,401, Jun. 11, 1982, abandoned.

[51] Int. Cl.$^4$ .................... B01J 13/00; C07C 143/24; C11C 1/00
[52] U.S. Cl. .................... 252/309; 260/505 N; 260/413
[58] Field of Search .................... 252/309; 260/505 N, 260/413 S

[56] References Cited

U.S. PATENT DOCUMENTS

| | | | |
|---|---|---|---|
| 2,144,808 | 1/1939 | Parker | 252/309 X |
| 2,846,392 | 8/1958 | Morway | 260/413 S |
| 3,231,592 | 1/1966 | McCord | 260/413 S |
| 3,251,869 | 5/1966 | Putnam | 260/413 S |
| 3,312,630 | 4/1967 | Vanik et al. | 252/309 |
| 3,634,476 | 1/1972 | Rinse | 260/413 S X |
| 3,803,188 | 4/1974 | Scott | 260/413 S |

FOREIGN PATENT DOCUMENTS

| | | | |
|---|---|---|---|
| 506315 | 10/1954 | Canada | 252/309 |
| 530460 | 9/1956 | Canada | 260/505 N |

Primary Examiner—Richard D. Lovering
Assistant Examiner—Catherine S. Kilby

[57] ABSTRACT

A process is provided for preparing colloidal dispersions of ceric dioxide in inert organic media which comprises
(1) heating
(a) ceric dioxide comprising ammonium nitrate or ammonium and nitrate ions in an amount within the range from about 3 to about 14% by weight of the ceric dioxide and a member selected from the group consisting of water, methanol, acetic acid and mixtures thereof in an amount usually from about 10 to about 60 g per mole of CeO$_2$, sufficient to effect reaction with
(b) an organic acid having from about ten to about forty carbon atoms
(c) an organic solvent selected from the group consisting of
(i) aliphatic and aromatic hydrocarbons, such as petroleum spirits, benzene, toluene, chlorobenzene, chlorotoluene, etc.
(ii) aliphatic and cycloaliphatic ethers, such as isopropyl ether or dicyclohexyl ether
(iii) aliphatic and cycloaliphatic ketones, such as diisobutylketone or cyclohexanone
at a temperature within the range from about 60 to about 200° C. thereby effecting dispersion of the ceric dioxide;
(2) removing water, methanol, acetic acid or mixtures thereof, and separating undissolved particles of solid material such as ammonium nitrate and undissolved cerium dioxide.

Association complexes are also provided, composed of ceric dioxide and organic acid having from about ten to about forty carbon atoms in a molar ratio CeO$_2$/organic acid of at least about 4:1.

25 Claims, 2 Drawing Figures

PROCESS FOR PREPARING COLLOIDAL CERIC OXIDE AND COMPLEXES THEREOF WITH FREE ORGANIC ACIDS

This application is a continuation-in-part of Ser. No. 387,401, filed June 11, 1982, and now abandoned.

Metal soaps are well known for their application as driers used in paint and varnish formulations, to accelerate the drying of unsaturated oils such as linseed oil or unsaturated synthetic resins such as alkyd resins. The metallic soap cation is assumed to actively catalyze the oxidation and polymerization processes, while the acid anion serves as a carrier for the metal, conferring oil-solubility, water-insolubility, and compatibility with the other components of the paint.

British Pat. No. 1,236,085 to Steel and Smith, published June 16, 1971, accordingly observes that it is obviously economically advantageous to incorporate as much metal per unit of acid as possible, providing the resulting soap is oil-soluble. This is achieved by the use of "basic" soaps, in which the ratio of metal to acid is greater than the stoichiometric ratio, for example:

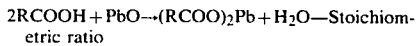
etric ratio

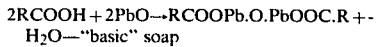
$H_2O$—"basic" soap

However, the patent comments that in the preparation of "basic" soaps of this type the resulting solution of soap and oil is so highly viscous as to be very difficult to handle, particularly in the blending operations necessary in the manufacture of paint compositions. According to the British patent, this high viscosity can be reduced by reacting the reaction mixture of the carboxylic acid or alkali metal salt thereof with a polyvalent metal salt or metal oxide providing the metal cation of the paint drier.

The polyvalent metal salt or metal oxide used in the process is a salt or oxide of aluminum, barium, copper, iron or magnesium, preferably of zirconium, zinc or manganese, and most preferably of calcium, lead or cobalt. Mixtures of different metal soaps are recommended, inasmuch as certain soaps such as the zinc and calcium soaps do not act as driers on their own, but exert a synergistic effect on other soaps, such as the cobalt or lead soaps. There is no reference to rare earth metal or cerium soaps.

British Pat. No. 972,804 to Turner, Downs and Harson, published Oct. 14, 1964, describes metal organic soaps which contain aluminum or boron and at least one divalent metal element or metal radical, the aluminum or boron and the divalent metal atoms being linked through oxygen atoms, and at least one carboxylic acid radical. Such metal organic compounds are obtained by condensing alkoxides or aryl oxides of aluminum or boron with acyl oxides of divalent metals or metal radicals. The divalent metals and metal radicals include magnesium, calcium, strontium, barium, zinc, cadmium, iron, cobalt, nickel, lead, copper, manganese and the zirconyl radical, but there is no reference to rare earth metals or radicals, such as cerium. The products have a high metal content, with organic acid radicals present in the proportion of 0.5 to 1.5 equivalents per metal atom. As a result, the products have a higher acid acceptance potential than conventional metallic soaps. These therefore are an example of the kind of "basic" soaps referred to in British Pat. No. 1,236,085, discussed above.

British Pat. No. 1,430,347 to Collins and Pearl, published Mar. 31, 1976, notes that the normal or "basic" metal soaps of synthetic carboxylic acids have been compounds analogous to those previously derived from natural acids, or, in using different synthetic carboxylic acids as they become available, have presented compounds with a more or less homologous if not isomeric relation to each other. Collins et al propose a departure from this prior art, using a different method of preparation, and a different composition, which results in a different character and properties of the resulting drier product or metal soap.

The prior art procedure according to Collins et al involves fusion or precipitation methods. The reactant acid can be dissolved in an appropriate inert solvent, usually a hydrocarbon solvent such as mineral spirits, to which then is added the desired metal compound, usually in the form of an appropriate oxide or inorganic compound or salt, with heating at an appropriate temperature to promote the reaction. This results in a hydrocarbon solution of the soap, and the solvent can be distilled off to increase the metal concentration to the desired value.

The Collins et al process utilizes a carboxylic acid or acid mixture which may be natural in origin, or derived from a natural product, or a synthetic product, and mixes this with a glycol ether or glycol or like polyol, with addition also of a metal compound such as the metal powder or an oxide, hydroxide, acetate, or carbonate of the metal. This mixture is then heated at a temperature from 65° to 143° C. until the metal compound disappears, after which water is distilled off, the reaction mixture filtered, and excess glycol and glycol ether distilled off to an appropriate desired concentration or condition.

The equivalents ratio of metal to glycol ether or polyol is at least 0.5, but a significant amount of the glycol ether or polyol must be retained in the product when it is desired to maintain fluidity. The equivalents ratio for the metal moiety and the acid moiety is at least 1.0, and when the metal is lead, at least 1.5, and ratios of 2 and higher are easily obtained for lead. Barium, nickel and manganese soaps as well as cobalt soaps have been prepared by this method, in addition to lead. There is however no reference to rare earth metals, such as cerium.

The patentees note that their product and process are clearly distinct from the use of varying amounts of glycol or glycol ether merely to reduce the viscosity of the lead carboxylate, as in British Pat. No. 1,148,998, or to stabilize soap solutions, as in Fisher U.S. Pat. No. 2,007,553. These products are marketed by the assignee, Mooney Chemicals, Inc.

Gamlen Europe SA, French Pat. No. 76 22426, publication No. 2,359,192, published Feb. 17, 1978, and British Pat. No. 1,571,210 published July 9, 1980, provides organic cerium salts soluble in organic solvents characterized by a ratio r of the number of acid equivalents to the number of cerium atoms of between 0.2 and 1, the number of acid equivalents meaning the number of acid molecules when the acid used is monofunctional, and this number has to be doubled or trebled in the case of diacids or triacids, and more generally multiplied by the number of acid functions in the case of a polyacid. The cerium compounds thus provided require a much smaller amount of acid than the amount used previously with the same effectiveness, and also solutions of high metal concentration reaching 500 g/l can be obtained which remain fluid and are capable of being handled without difficulty, while at the same time remaining completely soluble in hydrocarbon media.

The organic acid can be any of RCOOH, $RSO_3H$, $ROSO_3H$, $ROPO_3H_2$ or $(RO)_2PO_2H$, where R is a hydrocarbon radical having at least seven carbon atoms. The organic acid radical can be a linear or branched aliphatic radical or a cycloaliphatic radical, which is optionally alkylated, or an aromatic radical, which is optionally alkylated. The cerium organic acid salts may contain at least one other rare earth metal element, in addition, in an amount up to 25% of the total rare earth element content including cerium. These compositions can be provided in the form of organic solvent solutions of the cerium organic acid salt or mixture thereof containing more than 200 g/l of the composition. This composition can be included in paints or varnishes or liquid fuels.

The method for preparing these cerium organic acid salts or mixtures thereof comprises reacting (in organic or an aqueous organic medium) the organic acid and freshly prepared cerium hydroxide $Ce(OH)_3$ under such conditions that the resultant cerium organic acid salts have a ratio r of between 0.2 and 1. The reaction is preferably effected with heating, and preferably the organic medium is a hydrocarbon. After several hours, part of the water formed by the reaction separates spontaneously. After the reaction, to assist in the separation of water from the reaction medium, a further solvent can be added, such as a glycol, an alcohol or an alkyl glycol. The solution thus obtained can have its concentration adjusted by addition of a suitable hydrocarbon.

In the working Examples, cerium hydroxide $Ce(OH)_3$ is obtained by precipitating cerium nitrate with aqueous ammonia. The precipitate is washed with water until nitrate ion has disappeared, and then filtered until it contains only 15% water. The cerium hydroxide is reacted with 130 g of usual-grade oleic acid in white spirits at 80° C. After stirring for four hours, glycol is added, the separated water is eliminated, and then butyl-glycol is added, after which white spirit is added to form the final solution.

It will be noted that it is with the cerous salts, not the ceric salts, that the patentees are concerned.

French patent application No. 81 09214, U.S. Pat. No. 2,482,075, and related cases therein discussed refer to the preparation of aqueous dispersions of cerium compounds that can be easily dispersed. By heating hydrated ceria containing $NO_3^-$, $Cl^-$ or $ClO_4^-$ for 1 to 2 hours at temperatures of from 200° to 450° C., a material is obtained that is dispersible in aqueous solutions. No indications are given, however, that the material can be dispersed in organic media.

Kirk-Othmer, *Encyclopedia of Chemical Technology* (Second Edition), Volume 4, p. 850, indicate that hydrated ceric oxide, also referred to as hydrous ceric oxide or cerium hydroxide $CeO_2 \cdot xH_2O$, where x is a number from ½ to 2, forms as a gelatinous precipitate when sodium or ammonium hydroxides are added to solutions of ceric salts. It is usually referred to as hydrous ceric oxide. When the precipitate is dried, a yellow hydrated oxide containing 85 to 90% $CeO_2$ results. Granular ceric hydroxide may be made by boiling insoluble cerium salts with concentrated sodium hydroxide, followed by washing and drying. The composition and structure of these compounds depend on the method of preparation, and in many cases are uncertain. For this reason, it is common practice to express the composition in terms of equivalent $CeO_2$.

Cerous hydroxide $Ce(OH)_3$ forms as a white or off-white gelatinous precipitate when solutions containing cerous ion $Ce^{3+}$ are made alkaline. When allowed to stand for any length of time, a violet surface layer of cerosoceric hydroxide appears.

Ceric oxide $CeO_2$ usually is made by igniting cerous oxalate or cerous or ceric hydroxide in air. Ceric oxide is insoluble in acids, but dissolution is hastened by adding a small quantity of a reducing agent, such as an iodide or hydrogen peroxide. Eventually, strong nitric or sulfuric acid reacts upon heating.

In many applications, hydrated ceric oxide may be substituted for ceric oxide. However, unlike cerous hydroxide, which is a classic type of metal hydroxide similar to $Pb(OH)_2$, $Fe(OH)_3$, etc., ceric hydroxide is actually hydrated ceric dioxide, also called hydrous ceric oxide, as noted above. Accordingly, the term "ceric dioxide" as used in this specification and claims will be understood also to be inclusive of ceric hydroxide, hydrated ceric dioxide and hydrous ceric oxide, which are all different names for essentially the same chemical, ceric dioxide.

If pure ceric oxide is stirred and heated at a temperature in the range of from 60° to 200° C. in the presence of an aliphatic solvent, such as petroleum spirits, or an aromatic solvent, such as toluene, and in the presence of a carboxylic acid such as oleic, palmitic acid, or dodecylbenzene sulfonic acid, there is no dispersion. Neither is there any other reaction with any other carboxylic acid, or alkyl or alkylaryl sulphonic acid.

In accordance with the present invention, an entirely new type of high cerium content colloidal ceric dioxide is provided which can be dispersed in organic liquids, particularly organic solvents, as well as high cerium content compositions containing such colloidal ceric dioxide dispersed in an organic liquid. The high cerium content dispersions in accordance with the invention are true dispersions as demonstrated by transmission electron microscopy. The term "dispersed cerium dioxide" as used in this specification and claims indicates that the ceria particles are of colloidal dimensions, and therefore exist in the form of a colloidal dispersion in organic liquids, but this does not exclude the presence of ceria in solution, in addition to or instead of the colloidally dispersed ceria. Transmission electron microscopy of the hydrated ceria before treatment in accordance with the invention does not show particles of colloidal dimensions. The conversion of this ceria to colloidal size particles is obtained during the treatment.

Figure 2:
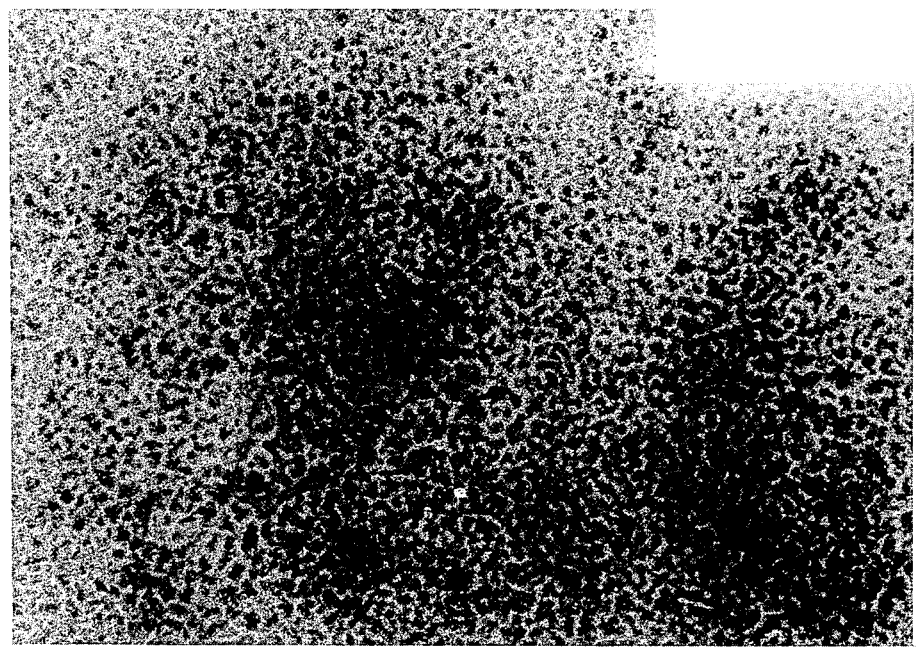

FIG. 1 is a transmission electron microphotograph showing the crystalline particle form of a typical ceric dioxide prior to treatment in accordance with the process of the invention; and FIG. 2 is a transmission electron microphotograph showing the particle form of the ceric dioxide of FIG. 1 after treatment in accordance with the process of the invention.

Colloidal ceric dioxide is obtained from ceric dioxide prepared especially for use as a starting material in the process of the invention in such a way as to contain in physical association therewith:

(1) from about 3 to about 14% of ammonium nitrate; and (2) at least one of water, methanol, acetic acid and mixtures of any two or three thereof in an amount within the range from about 10 to about 60 g per mole of CeO$_2$.

Both (1) and (2) are essential, and must be present. This material is referred to herein as "active ceric dioxide" or "active CeO$_2$".

It has been established by experimental evidence that the process of the invention can be regarded as effecting a physical adsorption-addition reaction (as contrasted to a chemical substitution-elimination reaction, such as a salt formation) of the organic acid, possibly interstitially, or as an inclusion by chemisorption, into the ceric dioxide, whether crystalline or noncrystalline. This association is formed upon the breakdown of the large agglomerates of ceric dioxide into crystallites with diameters of about 50 Å while heating the active ceric dioxide as above defined, and in the presence of a solubilizing organic acid of ten to forty carbon atoms and an appropriate organic liquid at a temperature within the range from about 60° to about 200° C., for a sufficient time, usually from 1 hour to about 24 hours, to effect the reduction of the agglomerates to colloidal size crystallites and their association with the solubilizing acid, followed by removal of the water, methanol or acetic acid released, and filtering off the salts that separate upon cooling.

The CeO$_2$-acid association complex can be isolated from such colloidal solutions in solid colloidal particle form. Transmission electron microscopy of the colloidal solutions shows perfectly dispersed crystallites of 50 Å. Provided it is kept in a closed container, the complex remains stable for some time. When mixed with an appropriate organic liquid, a colloidal dispersion is obtained at once.

The starting ceric dioxide can be pure ceric dioxide, hydrous ceric dioxide, or hydrated ceric dioxide, but it is essential that the ceria starting material contain from about 3 to about 14% by weight ammonium nitrate. The ammonium nitrate cannot be merely in admixture with or added to the ceria, but must be in close physical association with the ceria, possibly as an inclusion of ammonium nitrate as the salt molecule and/or as ammonium and nitrate ions in the structure of the agglomerates found in the course of preparation of hydrated ceria. The second requirement is the presence in the system of the indicated amount of water, or methanol, or acetic acid, or mixture thereof.

The starting ceric dioxide suitable for making the products of the invention is commercially available from Rhone-Poulenc. It can slso be prepared by processes described in the patents, for instance, cerous nitrate or cerous carbonate treated with aqueous nitric acid followed by NH$_4$OH—H$_2$O$_2$ treatment, as indicated in French patent publication No. 2,482,075. For the purpose of this invention, the ceric dioxide that is recovered, for example, by filtration, centrifuging, or other separation technique, does not need to be washed, but if washed, it is not washed sufficiently to remove the occluded ammonium nitrate. It thus has in physical association from about 3 to about 14% residual ammonium nitrate, and also some cerium nitrate. The amount of nitrate may vary, depending on the process parameters selected in the manufacture, the amount of residual mother liquor, or the extent of partial washing, if applied. Understandably, when the base used for the precipitation is NH$_4$OH, the ions carried by the ceria will be those of NH$_4^+$ and NO$_3^-$.

The wet material as it comes from the filter contains also a variable amount of water. If the second requirement is to be met by water present, it may be noted that at least about 10 g of water/mole of CeO$_2$ is necessary for the wet material to be useful in the invention. Normally, the amount of water retained in the freshly prepared hydrated ceria is from about 10 to 20%. Obviously, a higher water content can be present, but is a nuisance, since it has to be removed later on in the process.

Surprisingly, while methanol can be used in substitution for water, other lower alcohols such as ethanol are not effective, and cannot be substituted for the methanol.

Similarly acetic acid is the only acid that can be substituted for the water or the methanol; the organic acid used for preparation of the association complex cannot be used. The acetic acid as the water or the methanol has evidently a special function in the still not fully understood mechanism of breaking the agglomerates to colloidal size CeO$_2$, followed by the addition of the solubilizing acid.

The amount of water or methanol or acetic acid or mixture thereof is from at least 10 up to about 60 g/mole CeO$_2$.

Prolonged drying of the ceria should not be carried out at such high temperatures, as for instance at 375° C. or above, that ammonium nitrate decomposes, since then the NH$_4$NO$_3$ content in the resulting ceria could drop below the required minimum amount, and the resulting ceria material may no longer be useful in the process of the invention, even with the addition of water, methanol, or acid, and even free ammonium nitrate.

The organic liquid medium used in the process can be an inert aliphatic or cycloaliphatic hydrocarbon or mixture thereof, such as for example, mineral or petroleum spirits or mineral or petroleum ethers, which may also contain aromatic components. Examples include hexane, heptane, octane, nonane, decane, cyclohexane, cyclopentane, cycloheptane, and liquid naphthenes. Aromatic solvents, such as benzene, toluene, and the xylenes, are also suitable.

Chlorinated hydrocarbons such as chlorobenzene and chlorotoluene can also be used, as well as aliphatic and cycloaliphatic ethers, such as diisopropyl ether, and aliphatic and cycloaliphatic ketones. The organic liquid or solvent system will be selected taking into consideration the solubilizing organic acid that is used, and the heating temperature, as well as the ultimate application of the colloidal solution or dispersion. In some cases, a mixture of solvents is preferable. The amount of liquid or solvent evidently determines the final concentration. Solutions containing up to about 50% CeO$_2$ are perfectly fluid. It is therefore more economical and convenient to prepare more highly concentrated solutions which later on can be diluted for use. For this reason the amount of solvent is not critical.

The organic acid forming the physical association complex is an organic acid or a mixture of acids that is soluble in the organic solvent medium used. Aliphatic carboxylic acids, aliphatic sulphonic acids, aliphatic phosphonic acids, alkyl aryl sulphonic acids and alkyl aryl phosphonic acids having from about ten to about forty carbon atoms, natural or synthetic, can be used. Exemplary are tall oil fatty acids, oleic acid, stearic acid, isostearic acid, lauric acid, 2-ethylhexoic acid, naphthenic acid, hexoic acid, toluene sulphonic acid, toluene phosphonic acid, lauryl sulphonic acid, lauryl phosphonic acid, palmityl sulphonic acid, and plamityl phosphonic acid.

The type of solubilizing organic acid used often determines the maximum amount of $CeO_2$ that can be dissolved. Alkyl aromatic sulfonic acids tends to afford preparation of products having higher concentrations of Ce.

The organic acid is used in an amount of at least 0.25 mole per mole of $CeO_2$, inasmuch as the $CeO_2$-acid physical association complex contains a ratio of $CeO_2$:organic acid of 4:1, as evidenced by the composition of the isolated solid form. While smaller amounts of acid can be used, an incomplete dispersion of the ceria may result, or a relatively unstable dispersion that will tend to deposit $CeO_2$. More than 0.25 mole of organic acid can be used, but may not be necessary.

The presence of water, or methanol, or acetic acid, or mixture thereof is essential during the digestion time period, but their role is not well understood. At least it can be said that they assist in the expulsion of the nitrate ions in a manner resulting in the reduction of the $CeO_2$ agglomerations to colloidal size particles. The highly active surface of the crystallites then adsorbs the acid that renders them organo dispersible. If any of the essential activating volatile components, such as water, methanol, or acetic acid is removed from the system before the desired processes have taken place, the reaction may not take place at all, or can be incomplete.

Commercial grade hydrated ceria contain other rare earths as impurities. In some cases the presence of such impurities may be desirable for the beneficial synergistic effects they may exhibit. Mixtures of ceria containing up to about 10% of other rare earths can also be used in this process.

The overall heating can take from less than one hour up to about 24 hours or longer, while heating and agitating at a temperature within the range from about 60° to about 200° C.

A preliminary heating of the starting ceric dioxide either as an aqueous slurry or in a mixture with the organic liquid such as petroleum spirits at a temperature within the range from about 60° to about 200° C. for several hours followed by addition of the organic acid used in the formation of the physical association complex such as oleic acid results in significantly faster solubilization rates. Electron microscopic examination of the heated material has revealed that no size reduction of the ceria particles has taken place, and thus it is believed that during the heating the crystallite bridges of ammonium nitrate and/or $NH_4^+$ and $NO_3^-$ ions are weakened, but not broken. It appears that under the mild reaction conditions of the treatment, reduction of the ceria to colloidal size is effected by adsorption of the organic acid such as oleic acid onto the ceria particles, which also renders the colloidal particles dispersible in nonaqueous organic liquids or solvents. The colloidal dispersions produced by the described process thus is believed to contain the solubilizing acid as the free acid, and not in any ionized form. Thus, the cerium dioxide products described herein are not to be considered as cerium soaps, since these soaps are essentially cerium salts of ionized fatty acids.

The following Examples in the opinion of the inventors represent preferred embodiments of the invention.

EXAMPLE 1

In a 3-necked reaction flask equipped with a stirrer, thermometer and a condenser were charged 55 g of active $CeO_2$ containing 77.5% of $CeO_2$ (0.248 mole), 15.5% of water, and 7.0% of ammonium nitrate (as inclusions), 17.6 g of oleic acid (0.062 mole), and 35.0 g AMSCO solvent (aliphatic hydrocarbons). The mixture was stirred and slowly brought up to 90° C., and the temperature maintained for 2 hours with stirring. The reaction started at 55° to 60° C., as indicated by the appearance of water droplets. During this time the solid suspension of $CeO_2$ changed into a brownish colored colloidal solution containing visible water. Hexane was added, and the system azeotropically dried, whereby 8.5 g of water was collected. After removing most of the azeotroping agent, the dark brown colloidal solution was filtered. The $CeO_2$ content was 44%.

In contrast, pure cerium dioxide (99.5% $CeO_2$) was stirred in AMSCO solvent in the presence of oleic acid at from 90° to 140° C. without and with added water for 4 days, but no dispersion took place.

EXAMPLES 2 TO 21

Following the same procedure as in Example 1, using the same active $CeO_2$ and the same mole ratio of $CeO_2$ and acid, and solvent, but using the acid and solvent shown in Table I, the following ceria preparations were made. In all cases, complete dispersion of the ceria was achieved.

TABLE I

| Example No. | Solvent | Organic Acid | Reaction Temperature (°C.) | Reaction Time (hours) |
|---|---|---|---|---|
| 2 | Toluene | Stearic Acid | 87 | 4 |
| 3 | AMSCO | Isostearic | 103–106 | 1½ |
| 4 | AMSCO | Lauric acid + Oleic acid | 53–117 | 6 |
| 5 | Toluene | Dodecyl benzene Sulfonic acid | 90 | 6 |
| 6 | AMSCO | Linoleic acid | 60–101 | 0.45 |
| 7 | Dichlorobenzene | Oleic acid | 90 | 4 |
| 8 | AMSCO | Myristic acid | 62–118 | 6 |
| 9 | Diisobutyl ketone | Oleic acid | 100 | 1 |
| 10 | AMSCO | Coconut oil fatty acids | 100 | 4 |
| 11 | AMSCO | Soya oil fatty acids | 100 | 3.5 |
| 12 | p-chloro toluene | Oleic acid | 100 | 3 |
| 13 | AMSCO | Naphthenic acid | 90 | 6 |
| 14 | AMSCO | Tallow fatty acids | 85–93 | 1.5 |
| 15 | Diisobutyl ketone | Stearic acid | 85–100 | 4.5 |
| 16 | AMSCO | Linseed oil fatty acids | 70–104 | 1.5 |
| 17 | AMSCO | Capric acid | 88–115 | 4.5 |
| 18 | AMSCO | Octoic* and oleic acids | 85–90 | 1.0 |
| 19 | AMSCO | Pelargonic acid | 85–109 | 3.5 |
| 20 | Mesityl** oxide | Oleic acid | 47–90 | Overnight |
| 21 | Dibutyl ether | Oleic acid | 65–95 | Overnight |

*2 ethyl-hexoic acid
**with the addition of AMSCO to achieve clear solution.

EXAMPLE 22

Active $CeO_2$ containing 80.17% $CeO_2$, 2.9% $NH_4NO_3$, 16.9% $H_2O$, vacuum dried at 95° C., containing 3.1 g of residual water per mole of $CeO_2$, was attempted to be dispersed following the procedure of Example 1, using the same solvent and oleic acid, but no reaction or dispersion resulted. Then, 12 g of methanol was added per mole of $CeO_2$, and the mixture digested as in Example 1 for a period of 4 hours at 76° to 113° C.

Complete dispersion resulted. The methanol and the water were removed, yielding a colloidal solution or dispersion in AMSCO containing 45% of ceria.

EXAMPLES 23 TO 25

Active $CeO_2$ of the composition indicated in Example 22 that was oven-dried at 100° C. for 16 hours but still had a residual water amounting to 6.6 g/mole of $CeO_2$ was heated with 0.25 mole of oleic acid per mole of $CeO_2$ with or without additional amount of water and under the conditions outlined below in Table II.

TABLE II

| Example No. | Solvent | Total Amount of Water g/mole $CeO_2$ | Reaction Temperature (°C.) | Reaction Time (hours) |
|---|---|---|---|---|
| 23 | Toluene | 22 | 79–104 | 3.5 |
| 24 | AMSCO | 19.6 | 67–109 | Overnight (15 hours) |
| 25 | AMSCO | 6.6 | 50–140 | 48 |

Dispersion in Examples 23 and 24 was complete, but incomplete in Example 25. Example 25 thus indicates that 6.6 g water per mole of $CeO_2$ is on the borderline, as the dispersion was not complete.

EXAMPLES 26 TO 28

Active $CeO_2$ containing 75% $CeO_2$, 6.5% $NH_4NO_3$, 16.9% $H_2O$, was oven-dried at 175° C. for 72 hours. Oleic acid 0.25 mole/mole of $CeO_2$ was used as the organic acid under the conditions shown under Example 26.

Next, the dehydrated ceria was digested with added water (Example 27) or ethanol (Example 28) in the amount indicated in Table III for the time and at the temperature indicated in Table III.

TABLE III

| Example No. | Solvent | Added | g/mole of $CeO_2$ | Temp. (°C.) | Time (hours) |
|---|---|---|---|---|---|
| 26 | Toluene | None | — | 90–110 | 48 |
| 27 | AMSCO | Water | 33 | 55–90 | 4 |
| 28 | Toluene | Ethanol | 24 | 90–110 | 48 |

Only Example 27 went as desired to complete colloidal solution or dispersion. Example 26 did not contain water, and Example 28 had ethanol but not water or methanol, and neither gave any apparent dispersion of the ceria.

EXAMPLES 29 TO 30

Active $CeO_2$ of the preceding Examples 26 to 28 was azeotropically dried with toluene. Methanol (Example 29) or acetic acid (Example 30) was then added with oleic acid, and the dry powder was then dispersed under the conditions shown in Table IV.

TABLE IV

| Example No. | Solvent | Acid | Added | g/mole of $CeO_2$ | Reaction Temperature (°C.) | Reaction Time |
|---|---|---|---|---|---|---|
| 29 | Toluene | Oleic | MeOH | 10.0 | 74–88 | Overnight |
| 30 | Toluene | Oleic | Acetic Acid | 18.0 | 67–102 | Overnight |

EXAMPLE 31

The active $CeO_2$ of Example 1 was heated at 350° C. for 24 hours. The ceria was then mixed with AMSCO, oleic acid and water, and digested as in Example 27. No dispersion was observed after several days heating, even after adding methanol or acetic acid to the reaction mixture.

EXAMPLE 32

A 20 g sample of the colloidal solution prepared in Example 1 was slowly poured into 100 g acetone at room temperature. After stirring for a few hours at room temperature, the solid was filtered out and washed several times with acetone. The vacuum dried solid showed by analysis the following composition:
57.9% Ce
21.11% C
3.48% $H_2$
16.51% $O_2$ by difference
Empirical formula:
$Ce_4C_{18}H_{38}O_{10}$
Chemical Formula:
$(CeO_2)_4$(oleic acid)

The solid obtained as described is soluble in inert aliphatic or cycloaliphatic hydrocarbons, ketones and ethers, and chlorinated aromatic hydrocarbon solvents. The transmission electron microphotograph of this material is shown in FIG. 2. Although the acid is strongly adsorbed onto the surface of the ceria, a simple extraction with methanol yielded free acid in an amount of about 10% of the acid theoretically adsorbed.

This suggests that the oleic acid is adsorbed onto the surface of the ceria particles produced during the dispersion process. Support for this proposal was obtained from consideration of the infrared spectra obtained for the starting the final products. The carbonyl stretching vibration of free oleic acid was determined to be 1708 $cm^{-1}$, and this value is exactly in the range anticipated for a carboxyl group attached to an aliphatic chain. In the IR spectra of the mulled solid or original dispersion, no evidence for free oleic acid can be found. However, a strong (but broad) band is noted at 1510 $cm^{-1}$ (not due to solvent), and we assign this feature as being due to the perturbed carbonyl stretching mode of adsorbed oleic acid.

EXAMPLE 33

Commercial grade hydrated ceria containing 8.36% of ammonium nitrate and 21.34% total of water was stirred with oleic acid in AMSCO as in Example 1 at 90° C. Dispersion was achieved in 17 hours.

A sample of the same grade hydrated ceria (62.15 g) was mixed with 14.4 g of water and heated at 90° to 100° C. for 5 hours. The excess of water was removed by filtration, 17.59 g of oleic acid and 34.95 g of AMSCO were added, and the mixture was heated at 90° C. The dispersion was accomplished in 4 hours instead of 17.

One hundred gram sample of the hydrated ceria used in Example 33 was heated at 400° C. for 16 hours, resulting in 71.8 g dry powder containing 70.3 g cerium dioxide and 1.5 g of nitrates.

Mixing 43.9 g of the dried material with AMSCO and oleic acid with or without water gave no dispersion after 24 hours of heated at 90° C.

EXAMPLE 34

A sample of the active $CeO_2$ used in Example 4 was heated in AMSCO only for 6 hours at 90° C., and then the oleic acid added. The dispersion was total in 1.5 hours after the addition of the acid.

Having regard to the foregoing disclosure, the following is claimed as the inventive and patentable embodiments thereof:

1. A process for preparing colloidal dispersions of ceric dioxide in inert organic liquids which comprises
(1) heating
   (a) ceric dioxide containing ammonium nitrate in an amount within the range from about 3 to about 14% by weight of the ceric dioxide and a member selected from the group consisting of water; methanol; acetic acid; and mixtures thereof in an amount of at least 10 g per mole of $CeO_2$ sufficient to effect reaction with
   (b) an organic acid having from about ten to about forty carbon atoms; and
   (c) an organic liquid selected from the group consisting of aliphatic and aromatic hydrocarbons; aliphatic and cycloaliphatic ethers; and aliphatic and cycloaliphatic ketones at a temperature within the range from about 60° to about 200° C., thereby forming a colloidal dispersion in the organic liquid of the ceric dioxide and associated organic acid; and
(2) removing any water, methanol and acetic acid released durig the heating and separating any undissolved solid particles.

2. A process according to claim 1 in which water is used.

3. A process according to claim 1 in which methanol is used.

4. A process according to claim 1 in which a mixture of water and methanol is used.

5. A process according to claim 1 in which acetic acid is used.

6. A process according to claim 1 in which a mixture of water and acetic acid is used.

7. A process according to claim 1 in which a mixture of water, methanol and acetic acid is used.

8. A process according to claim 1 in which the organic liquid is an aliphatic hydrocarbon.

9. A process according to claim 1 in which the organic liquid is an aromatic hydrocarbon.

10. A process according to claim 1 in which the organic liquid is an aliphatic or cycloaliphatic ether.

11. A process according to claim 1 in which the organic liquid is an aliphatic or cycloaliphatic ketone.

12. A process according to claim 1 in which the organic acid is oleic acid.

13. A process according to claim 1 in which the organic acid is lauric acid.

14. A process according to claim 1 in which the organic acid is an alkyl sulfonic or alkyl aromatic sulfonic acid.

15. A process according to claim 1 in which the organic acid is isostearic acid.

16. A process according to claim 1 in which the organic acid is tallow fatty acids.

17. A process according to claim 1 in which the organic acid is linseed oil fatty acids.

18. A process according to claim 1 in which the organic acid is benzene sulfonic acid.

19. A process according to claim 1 in which the amount of water, methanol or acetic acid is within the range from about 10 to about 60 g per mole of $CeO_2$.

20. A process according to claim 1 which comprises heating the ceric dioxide comprising ammonium nitrate in the presence of water or the organic liquid at a temperature within the range from about 60° to about 200° C. and then adding the organic acid to the resulting mixture.

21. A process according to claim 20 in which the ceric dioxide is in the form of an aqueous slurry.

22. A process according to claim 20 in which the ceric dioxide is in the form of a slurry in the organic liquid.

23. A process according to claim 22 in which the organic liquid is an aliphatic hydrocarbon.

24. A process according to claim 22 in which the organic acid is oleic acid.

25. A colloidal dispersion is an organic solvent prepared by the process according to claim 1.

* * * * *